(12) United States Patent
Zhang

(10) Patent No.: US 9,277,889 B2
(45) Date of Patent: Mar. 8, 2016

(54) PATIENT SIGNAL ANALYSIS BASED ON ACTINIFORM SEGMENTATION

(71) Applicant: Siemens Medical Solutions USA, Inc., Malvern, PA (US)

(72) Inventor: Hongxuan Zhang, Palatine (IL)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 14/520,378

(22) Filed: Oct. 22, 2014

(65) Prior Publication Data

US 2015/0164429 A1 Jun. 18, 2015

Related U.S. Application Data

(60) Provisional application No. 61/916,330, filed on Dec. 16, 2013.

(51) Int. Cl.

| | |
|---|---|
| *A61B 5/046* | (2006.01) |
| *A61B 5/00* | (2006.01) |
| *A61B 18/14* | (2006.01) |
| *A61B 5/0456* | (2006.01) |
| *A61N 1/365* | (2006.01) |
| *A61N 1/39* | (2006.01) |
| *A61B 5/0464* | (2006.01) |
| *A61B 5/0472* | (2006.01) |

(52) U.S. Cl.
CPC .............. *A61B 5/7235* (2013.01); *A61B 5/046* (2013.01); *A61B 5/0456* (2013.01); *A61B 5/0464* (2013.01); *A61B 18/1492* (2013.01); *A61N 1/365* (2013.01); *A61N 1/3906* (2013.01); *A61B 5/0472* (2013.01); *A61B 5/4836* (2013.01)

(58) Field of Classification Search
None
See application file for complete search history.

(56) References Cited

U.S. PATENT DOCUMENTS

| | | | |
|---|---|---|---|
| 4,721,114 | A | 1/1988 | DuFault et al. |
| 4,802,491 | A | 2/1989 | Cohen et al. |
| 5,215,099 | A | 6/1993 | Haberl et al. |
| 5,782,876 | A | 7/1998 | Flammang |
| 5,810,722 | A | 9/1998 | Heikkila |
| 6,128,526 | A | 10/2000 | Stadler et al. |
| 6,169,919 | B1 | 1/2001 | Nearing et al. |
| 6,266,561 | B1 | 7/2001 | Gliner |
| 6,280,391 | B1 | 8/2001 | Olson et al. |
| 6,304,772 | B1 | 10/2001 | Taha et al. |
| 6,480,733 | B1 | 11/2002 | Turcott |
| 6,501,983 | B1 | 12/2002 | Natarajan et al. |
| 6,609,023 | B1 | 8/2003 | Fischell et al. |
| 6,785,573 | B2 | 8/2004 | Kovtun et al. |
| 6,819,953 | B2 | 11/2004 | Yonce et al. |
| 6,850,796 | B1 | 2/2005 | Mortara |
| 6,947,789 | B2 | 9/2005 | Selvester et al. |
| 7,066,891 | B2 | 6/2006 | Stadler et al. |
| 7,181,268 | B2 | 2/2007 | Sheldon et al. |
| 7,270,662 | B2 | 9/2007 | Visram et al. |
| 7,277,745 | B2 | 10/2007 | Natarajan et al. |

(Continued)

*Primary Examiner* — Kennedy Schaetzle

(57) ABSTRACT

Disclosed herein is a framework for facilitating patient signal analysis. In accordance with one aspect, actiniform segmentation is performed on patient signal data waveform based on an actiniform shape. The actiniform shape is centered at a peak of the waveform and includes connection lines extending from the peak to key time points of the patient signal data waveform. Actiniform parameters may be extracted from the segmented patient signal data waveform. Additionally, one or more actiniform ratios may be determined based on the actiniform parameters to monitor changes in the patient signal data waveform.

25 Claims, 6 Drawing Sheets

(56) References Cited

U.S. PATENT DOCUMENTS

| | | |
|---|---|---|
| 7,386,340 B2 | 6/2008 | Schlegel et al. |
| 7,412,283 B2 | 8/2008 | Ginzburg et al. |
| 7,539,535 B1 | 5/2009 | Schlegel et al. |
| 7,542,794 B1 | 6/2009 | Zhang et al. |
| 7,996,084 B2 | 8/2011 | Stylos et al. |
| 8,126,549 B2 | 2/2012 | Sigg et al. |
| 8,233,972 B2 | 7/2012 | Zhang |
| 8,265,740 B2 | 9/2012 | Fischell et al. |
| 8,275,457 B1 | 9/2012 | Fischell et al. |
| 8,364,248 B2 | 1/2013 | Zhang |
| 2007/0177770 A1* | 8/2007 | Derchak ............ G06K 9/00486 382/115 |

* cited by examiner

PATIENT SIGNAL ANALYSIS BASED ON ACTINIFORM SEGMENTATION

CROSS-REFERENCE TO RELATED APPLICATION

This application claims the benefit of U.S. provisional application No. 61/916,330 filed on Dec. 16, 2013, the entire contents of which are incorporated herein by reference.

TECHNICAL FIELD

The present disclosure generally relates to systems and methods for analyzing and characterizing patient signals.

BACKGROUND

Coronary artery disease (CAD) is one of the top killer diseases in today's society, accounting for nearly 500,000 deaths in America each year. Studies estimate that 50% of men and 33% of women under the age of 40 will develop some form of CAD sometime during their lifetimes. Sudden cardiac death has steadily accounted for approximately 50% of all heart-related, out-of-hospital deaths and improved clinical procedures almost entirely ignore this group. The fact that patients generally fail to recognize their symptoms and seek prompt medical attention contributes to this tragic statistic. However, the early stages of CAD are usually non-symptomatic and even invisible with current clinical cardiac signal analysis strategies. If fatal cardiac arrhythmia events can be sensitively and accurately detected and captured, the cardiac functional abnormality frequency and severity can be earlier detected and characterized. This may greatly help the doctor to provide early and more effective clinical treatment and then prevent fatal heart diseases.

Recognition and characterization of early arrhythmia events, such as ventricular tachycardia, myocardial ischemia (MI) and infarction, are critical for rhythm management of the cardiac disorders and irregularities. Currently, waveform morphology and time domain parameter analysis of depolarization and repolarization of cardiac signals, such as P wave, QRS complex, ST segment and T wave, are used for monitoring and identifying cardiac arrhythmia. However, such current clinical methodologies are sometimes subjective and time-consuming, and require expertise and clinical experience for accurate interpretation and proper cardiac rhythm management.

Recently, some research efforts have started to apply more sophisticated mathematical theories to interpret patient signal, such as frequency analysis, symbolic complexity analysis and nonlinear entropy evaluation, focusing primarily on generating a new pathology index for qualitative cardiac arrhythmia characterization. Although these research efforts may be able to qualitatively describe the pathology or event, they cannot provide enough information on cardiac electrophysiological function/activity interpretation, tissue mapping, arrhythmia localization, etc.

Additionally, traditional medical methods usually focus on changes in the time (amplitude, latency, etc.) or frequency (power, spectrum, etc.) domain, which may not efficiently and accurately capture minute signal changes in a partial portion (P wave, QRS complex, ST segment, etc.) of a cardiac cycle. Such changes are usually invisible in the signal wave morphology display or need extensive clinical expertise to obtain an accurate diagnosis. Consequently, a high failure rate of arrhythmia diagnosis and false negatives (FN) may result. A false negative (FN) wrongly indicates that a person has disease X (e.g., myocardial ischemia), even though he or she does not actually have the disease.

Known clinical approaches for cardiac arrhythmia identification and analysis based on electrocardiography (ECG) signals are subjective and require extensive expertise and clinical experience for accurate interpretation and appropriate cardiac rhythm management. More objective analytical and diagnostic strategies for cardiac signals and activities are needed. Furthermore, known methods based on amplitude (or voltage) variation analysis may not be sufficient for cardiac function evaluation and pathology diagnosis. No quantitative clinical evaluation and link between myocardial ischemia event/status and the amplitude and variation index are provided.

Known clinical evaluations for cardiac malfunction detection and characterization (e.g., MI and infarction) are based on the "golden standard" using ST segment voltage deviation (e.g., 0.1 mV elevation is the clinical standard for myocardial ischemia or MI detection). However, there are at least two shortcomings with the golden standard for this kind of diagnosis and evaluation: (a) this standard only works for surface ECG signals, but not for intra-cardiac electrograms (ICEG); (b) ST segment deviation in voltage cannot be utilized to quantitatively characterize myocardial ischemia severity. There is a clinical need for both quantitative and qualitative approaches for cardiac arrhythmia detection and characterization.

Further, current clinical methods based on cardiac pathology information extraction (e.g., atrial fibrillation or AF detection and MI diagnosis) may not be able to qualitatively and quantitatively capture minute changes, and predict the pathological trend, especially in the early stage of tissue malfunctioning and acute cardiac arrhythmia. Known current methods may not efficiently analyze the real-time growing trend of cardiac arrhythmias, such as the pathology trend from low risk to medium risk, and then to high risk (severe and fatal) rhythm (especially for some fatal arrhythmia, such as VT growing and trend to VF).

Even further, known clinical methods and strategies for cardiac pathology event detection and evaluations rely only on partial portion cardiac waveform and electrophysiological procedure, such as ST segment changes for myocardial ischemia. However, different portions of the cardiac waveform may provide some additional information of the events and cardiac diseases.

In addition, there are many cardiac arrhythmia (such as ischemia and fibrillation) analysis methods for detecting and treating heart pathology, such as heart rate variability, medicine, implantable cardioverter, etc. However, the efficiency and reliability of these kinds of clinical approaches may not be sufficient, especially in a noisy environment since atrial activities may be buried in noise and artifacts. It would be a challenge to efficiently and reliably extract atrial arrhythmia information from the electrophysiological signals (e.g., surface ECG and intra-cardiac electrograms). Current medical applications also need better methods to detect cardiac pathology events in a more reliable and timely manner, and particularly to provide early warning and treatment options for fatal heart arrhythmia, which can be used in implantable cardioverter defibrillator (ICD) patients.

SUMMARY

The present disclosure relates to a framework for facilitating patient signal analysis. In accordance with one aspect, actiniform segmentation is performed on patient signal data waveform based on an actiniform shape. The actiniform shape is centered at a peak of the waveform and includes connection lines extending from the peak to key time points of the patient signal data waveform. Actiniform parameters may be extracted from the segmented patient signal data waveform. Additionally, one or more actiniform ratios may be determined based on the actiniform parameters to monitor changes in the patient signal data waveform.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
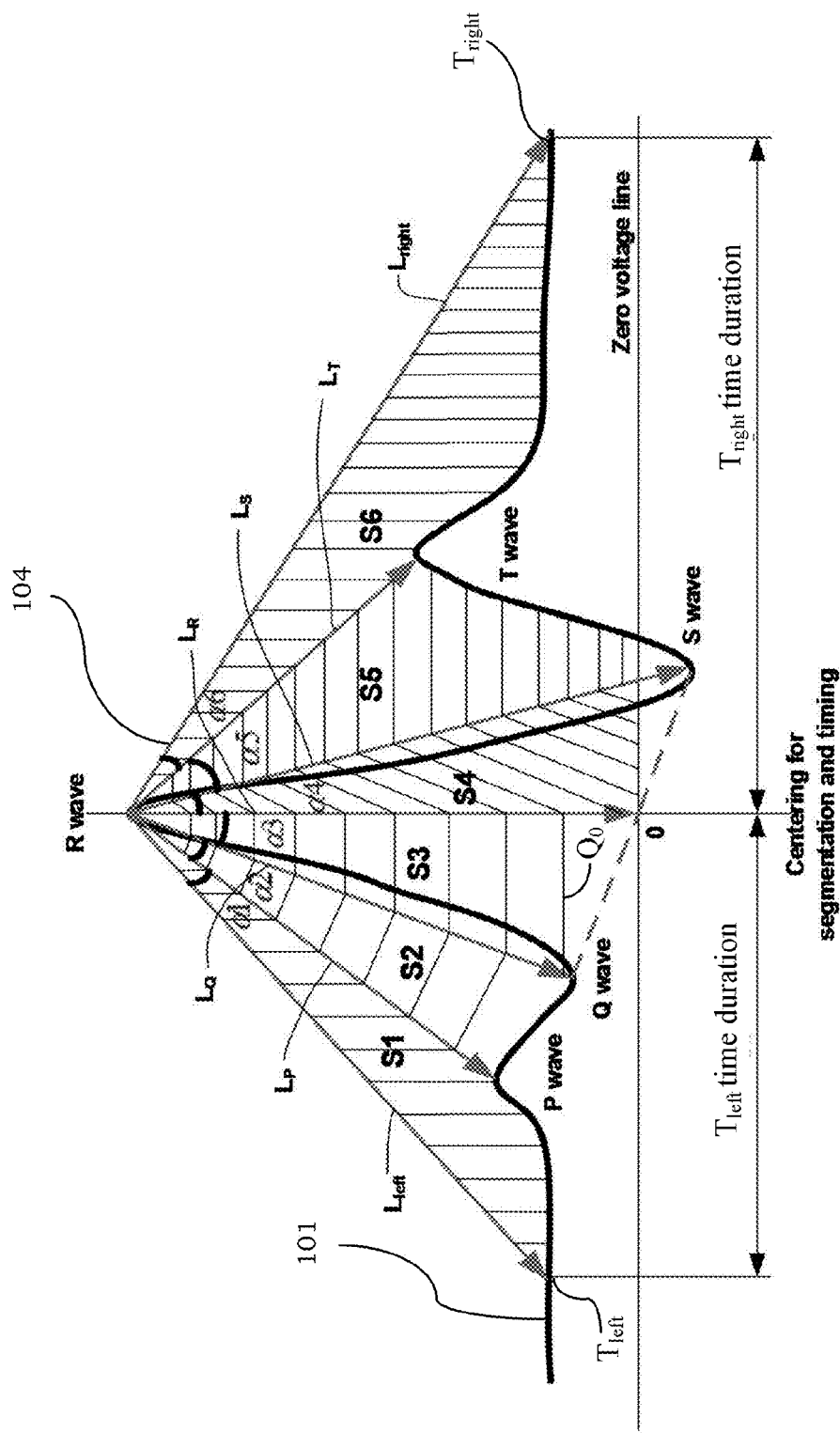
FIG. 1 illustrates an exemplary actiniform segmentation of an electrophysiological signal waveform.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

It is to be further understood that since the constituent system modules and method steps depicted in the accompanying Figures are preferably implemented in software, the actual connections between the system components (or the flow of the process steps) may differ depending upon the manner in which the present invention is programmed. Given the teachings herein, one of ordinary skill in the related art will be able to contemplate these and similar implementations or configurations of the present invention.

The present framework provides a methodology to analyze patient signals. In accordance with one aspect, the framework characterizes cardiac electrophysiological function signals (e.g., surface ECG signals, intra-cardiac electrograms, etc.) by segmenting or categorizing the signal waveforms into several different portions based on an actiniform (i.e., radiated) distribution pattern. Different portions of the cardiac electrophysiological signals represent activities of different cardiac tissue and circulation system. Based on such actiniform segmented cardiac activity, heart electrophysiological response and signal abnormality may advantageously be detected much earlier. The segmented electrophysiological signal analysis may be used to continuously monitor and capture minute changes of early stages of the CAD (especially for MI, AF, VT, etc.), which may help medical doctors to save time and reduce risk to cardiac patients by providing on-time treatment and drug delivery. Cardiac functionality and electrophysiological activities may be more reliably characterized to, for example, identify heart function disorders, differentiate cardiac arrhythmias, characterize myocardial pathological severities and tissue location, predict life-threatening events, evaluate drug delivery and effects, and so forth.

FIG. 1 illustrates an exemplary actiniform segmentation of an electrophysiological signal waveform 101. Different kinds of actiniform segmentations and different definitions of actiniform parameters, ratios and/or indices may be derived from the segmented waveform. As shown, the electrophysiological signal waveform 101 is segmented (or categorized) into different portions by an actiniform shape (or distribution) 104. In accordance with some implementations, the actiniform shape 104 is a non-uniform radiated form centered at an R wave peak. The actiniform shape 104 may also be centered at other time points or amplitude, depending on the clinical application or purpose. The actiniform shape 104 may be isotropic in different directions, speeds, strength, shapes and/or lengths.

The actiniform shape 104 includes connection lines extending from the center towards key time points of the signal waveform 101. The key time points may be defined based on different waves that occur within a cardiac cycle (e.g., P, Q, R, S, T waves, etc.). As shown, the cardiac cycle may be divided by the actiniform lines into six portions (S1 to S6) by using the time points corresponding to the P wave maximum amplitude (or peak), Q wave minimum amplitude, R wave maximum amplitude, S wave minimum amplitude, T wave maximum amplitude, $T_{left}$ and $T_{right}$ time points. $T_{left}$ is a time point defined before the occurrence of the P wave, while $T_{right}$ is a time point defined after the occurrence of the T wave. The $T_{left}$ and $T_{right}$ time durations may be measured from the R time point corresponding to the maximum amplitude (or mid-point) of the R wave to the $T_{left}$ and $T_{right}$ time points respectively. $T_{left}$ and $T_{right}$ time points may be predefined or determined by clinical users. Alternatively, they may be adaptively and automatically controlled by an algorithm. For example, when the heart rate is 60-80 beats per minute (BPM), $T_{left}$ and $T_{right}$ time durations may be set to 150 mS and 200 mS respectively. When the heart rate is higher, the corresponding $T_{left}$ and $T_{right}$ time durations may be proportionally decreased to adapt to cardiac cycle changes. By using R wave peak connection with every key time point, different actiniform line series $L_x$ may be derived: $L_{left}$, $L_P$, $L_Q$, $L_R$, $L_S$, $L_T$, and $L_{right}$. Different actiniform areas Sx may be defined based on these actiniform lines. For example, S3 is the area defined by $L_Q$, $L_R$, and $Q_O$ lines. Each area Sx may be represented by a set of data points within and/or around the actiniform area.

Segmentation may be based on other key time points, such as the U wave point, zero voltage cross point, etc. Accordingly, any portion of the cardiac signal may be accurately and reliably monitored and visualized. Based on the clinical application and diagnosis needs, the segmentation may be simplified by selecting certain connection lines or areas of interest, such as S1, S2, and S3 for atrial chamber abnormality and pathology detection. Similarly, the angles ($\alpha 1$, $\alpha 2$, etc.) between the actiniform lines may be adaptively and automatically measured. The angle values may be utilized for monitoring and calculating cardiac signal waveform shape distortion and changes.

Figure 2:
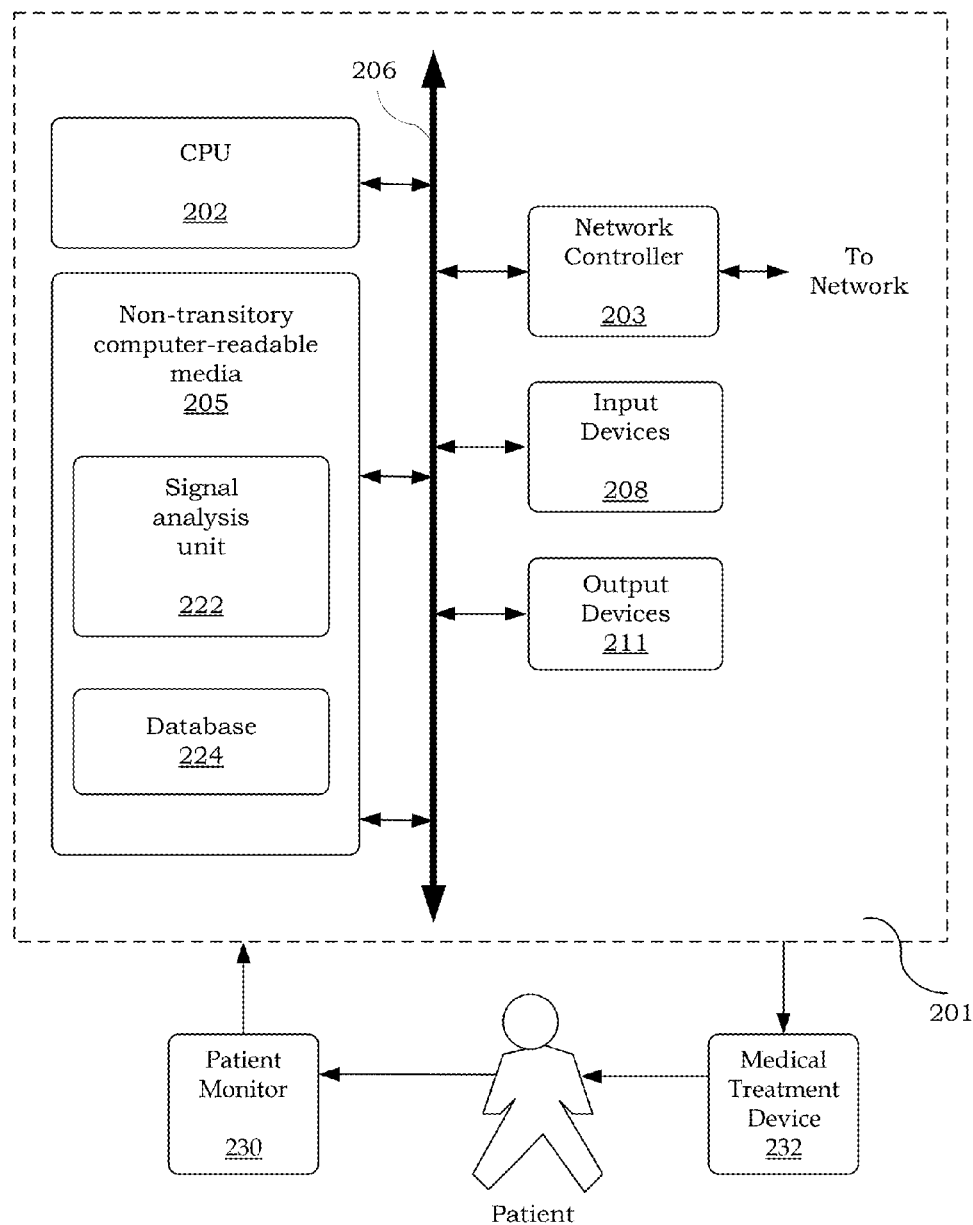
FIG. 2 shows an exemplary system.

FIG. 2 shows an exemplary system 200 for implementing a method and system of the present disclosure. It is to be understood that, because some of the constituent system components and method steps depicted in the accompanying figures can be implemented in software, the actual connections between the systems components (or the process steps) may differ depending upon the manner in which the present framework is programmed. For example, the system 200 may be implemented in a client-server, peer-to-peer (P2P) or master/slave configuration. In such configurations, the system 200 may be communicatively coupled to other systems or components via a network, such as an Intranet, a local area network (LAN), a wide area network (WAN), a P2P network, a global computer network (e.g., Internet), a wireless communications network, or any combination thereof. Given the teachings of the present invention provided herein, one of ordinary skill in the related art will be able to contemplate these and similar implementations or configurations of the present invention.

As shown in FIG. 2, the system 200 may include a computer system 201, a patient monitor 230 and a medical treatment device 232. The computer system 201 may include, inter alia, a central processing unit (CPU) 202, a non-transitory computer-readable media 205, one or more output devices 211 (e.g., printer, display monitor, projector, speaker, etc.), a network controller 203, an internal bus 206 and one or more input devices 208, for example, a keyboard, mouse, touch screen, gesture and/or voice recognition module, etc. Computer system 201 may further include support circuits such as a cache, a power supply, clock circuits and a communications bus. Various other peripheral devices, such as additional data storage devices and printing devices, may also be connected to the computer system 201.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein may be implemented as computer-readable program code tangibly embodied in non-transitory computer-readable media 205. Non-transitory computer-readable media 205 may include random access memory (RAM), read only memory (ROM), magnetic floppy disk, flash memory, and other types of memories, or a combination thereof. The present techniques may be implemented by patient signal analysis unit 222 that is stored in computer-readable media 205. As such, the computer system 201 is a general-purpose computer system that becomes a specific purpose computer system when executing the computer-readable program code.

The same or different computer-readable media 205 may be used for storing a database 224. Database 224 may include a repository of determined parameters and ratios, selectable predetermined functions, patient signal data (e.g., electrophysiological, ECG, ICEG, respiration signal data, other hemodynamic or vital sign data, etc.), patient data (e.g., demographic data, pathology history, etc.), other input data and/or other derived output parameters. Patient signal data may be provided by a patient monitor 230 that is communicatively coupled to the computer system 201.

Patient monitor 230 may be used to acquire various types of patient biometric or electrophysiological signal information for monitoring the patient. For example, the monitoring information may include, but is not limited to, electrophysiological signal data (e.g., ECG, ICEG, etc.), oximetric or SPO2 signal data, respiration signal data, blood pressure, temperature and/or other patient biometric, physiological, hemodynamic, vital sign or medical parameter information. The patient monitor 230 may include appropriate biometric sensors (e.g., leads for surface ECG and basket catheter for intra-cardiac electrographic signal data) for acquiring the monitoring patient signals. Implementations of the present framework provide parameters to detect, diagnose and quantify such patient signals.

Medical treatment device 232 may be automatically and adaptively controlled by the computer system 201 in a closed loop feedback control system. Medical treatment device 232 may include, but are not limited to, a pacing device, ablator, cardioverter, defibrillator, and so forth. Control parameters of the medical treatment device 232, such as the pacing parameter, ablation energy control, etc., may be automatically determined by computer system 201.

Figure 3:
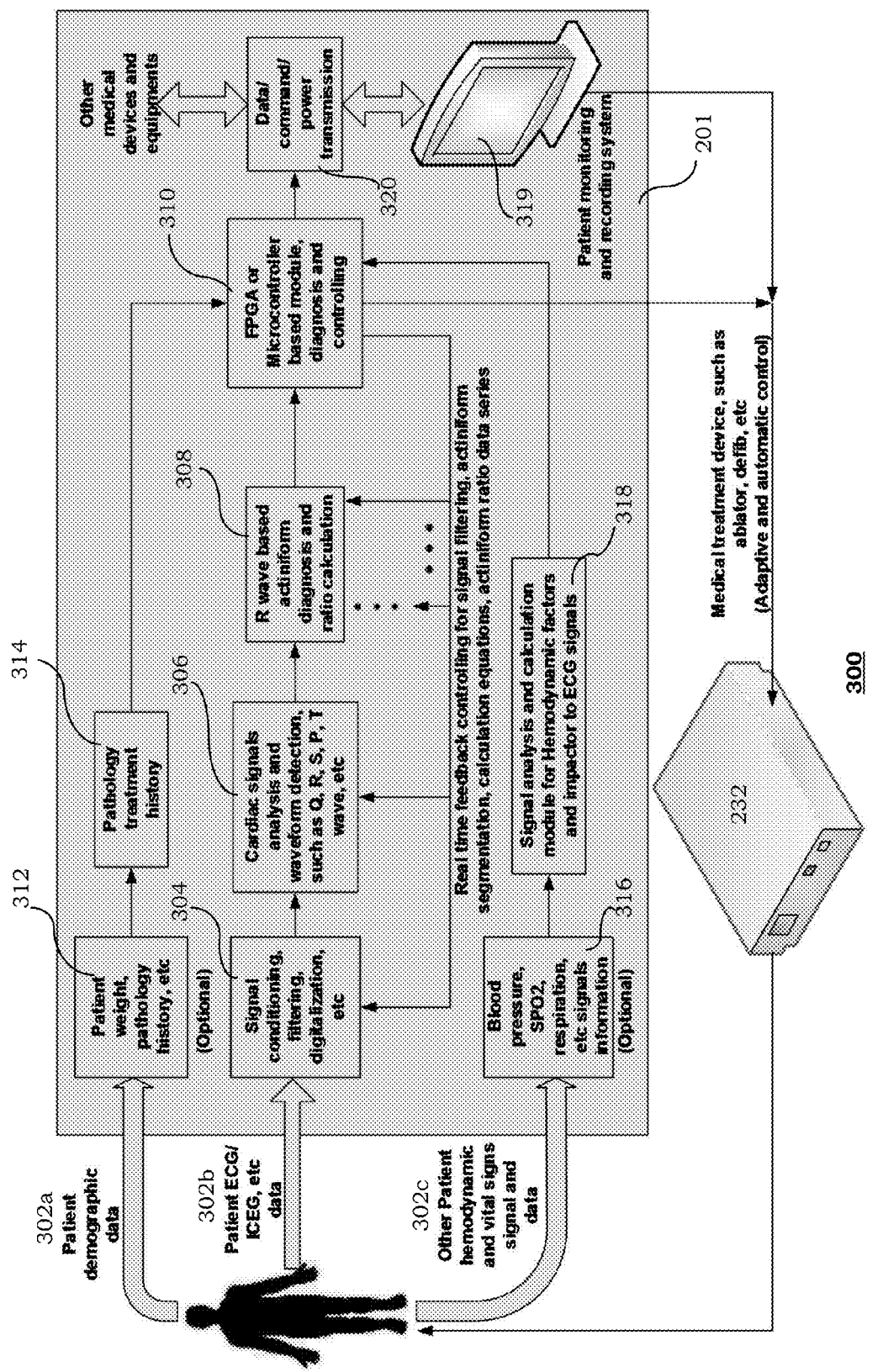
FIG. 3 shows an exemplary implementation of a closed loop feedback control system.

FIG. 3 shows an exemplary implementation of a closed loop feedback control system 300. As shown, different kinds of patient information, such as demographic information 302a, patient weight, pathology history 312, pathology treatment history 314, other patient hemodynamic or vital sign data 302c, blood pressure, oximetric (or SPO2) data, respiration signal data 316, hemodynamic factors derived from such signal data 318, etc. may be integrated with actiniform calculation and characterization to provide better accuracy and reliability in characterizing cardiac arrhythmia location, severity, treatment priority, controlling external medical treatment, etc.

In accordance with some implementations, computer system 201 samples patient electrophysiological signal data 302b (e.g., surface ECG or intra-cardiac electrographic data after signal filtering and conditioning at 304). Signal analysis unit 222 detects the waves within the signal data (e.g., P wave, R wave, Q wave, S wave, T wave, etc.) at 306. Signal analysis unit 222 further performs R wave-centered actiniform segmentation for patient signal timing (peaks and valleys) and derives different kinds of actiniform parameters, ratios, indices, etc., at 308. Different kinds of actiniform ratios may be derived for same or cross cardiac cycle waveform diagnosis, such as unilateral and bilateral actiniform ratios, as will be discussed in more detail in the following description. The actiniform ratios may be calculated sequentially for statistical verification of cardiac status pattern and mode monitoring. Such computations may be executed by a field-programmable gate array (FPGA) or microcontroller 310. The derived actiniform parameters, ratios and/or indices may be used in characterizing the severity, type, location, treatment priority, etc., of cardiac arrhythmia. FPGA or microcontroller 310 or patient monitoring and recording system 319 may send control parameters or power transmission 320 to external medical treatment devices 232 (e.g., pacing device, ablator, cardioverter, defibrillator, etc.) and/or other medical devices or equipment in real-time. In addition, a closed-loop feedback may be provided to adaptively adjust calculation control parameters for the different steps 304, 306 and 308.

Figure 4:
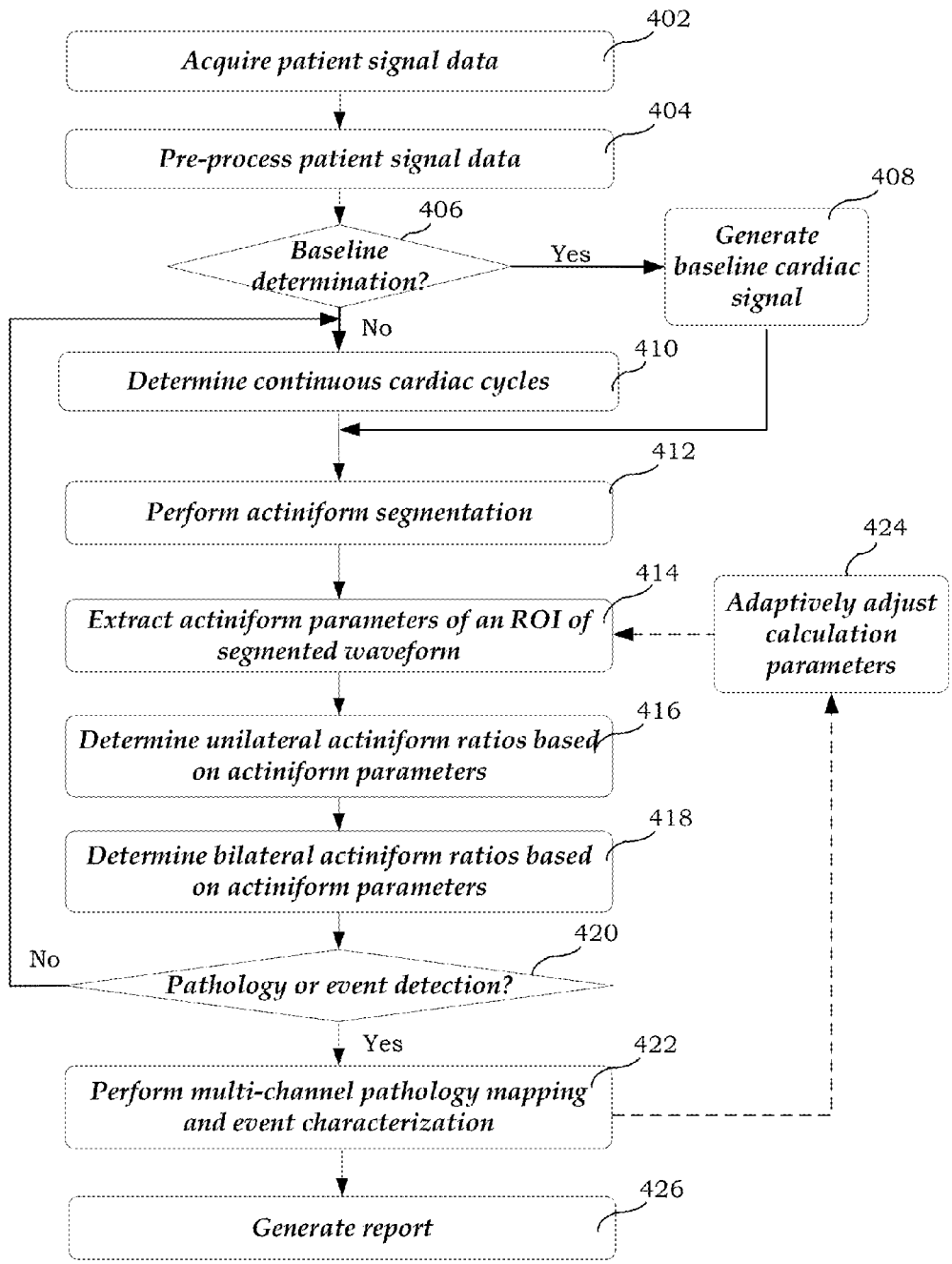
FIG. 4 shows an exemplary method of analyzing patient signals based on actiniform segmentation.

FIG. 4 shows an exemplary method 400 of analyzing patient signals based on actiniform segmentation. The steps of the method 400 may be performed in the order shown or a different order. Additional, different, or fewer steps may be provided. Further, the method 400 may be implemented with the system 200 of FIG. 2, system 300 of FIG. 3, a different system, or a combination thereof.

At 402, patient monitor 230 acquires patient signal data from a current patient. In some implementations, the patient signal data comprises cardiac electrophysiological signal data, such as intra-cardiac electrographic (ICEG) data, surface ECG data, etc. The cardiac electrophysiological signal data may be acquired by multiple channels connected to an intra-cardiac basket catheter placed into, for example, the right atrium of the heart. Alternatively, or additionally, other types of electrophysiological signal data, such as hemodynamic (HEMO) signal data, respiration (or capnographic) signal data, blood pressure data, oximetric (SPO2) data, and/or other vital sign signal data, other measurable patient biometric, physiological or medical signals, may also be acquired. In addition, other patient information, such as demographic data, clinical application and patient status, including, but not limited to, weight, height, gender, age, allergies, medications, pathology history, pathology treatment history, etc., may also be acquired.

At 404, the patient signal data is pre-processed. The patient signal data may be pre-processed by conditioning, filtering, amplification, digitization and/or buffering. For example, the patient signal data may be pre-filtered and amplified for display on, for instance, patient monitor 230. The patient signal data may be filtered to remove unwanted patient movement and respiratory artifacts, as well as power line noise. The filter may be adaptively selected in response to data indicating clinical application (e.g. ischemia detection application, rhythm analysis application). The patient signal data may be conditioned, amplified, buffered, filtered and/or digitized to produce a continuous stream of digitized samples.

At 406, patient signal analysis unit 222 may determine whether a baseline value or signal is to be automatically extracted from the digitized patient signal data. The baseline value (or signal) generally refers to a known threshold value (or benign signal) with which an unknown value (e.g., amplitude) is compared when measured or assessed. The baseline value may be used in, for example, threshold determination, computation of actiniform parameters (e.g., cross ratios), and so forth.

If the baseline value or signal is to be automatically determined, at 408, patient signal analysis unit 222 automatically generates the baseline cardiac value or signal. The baseline value may comprise a zero voltage line if a static (DC) voltage signal component is filtered out from the signal. The baseline value may be adaptively adjusted according to the current application and clinical requirements. Alternatively, if the value is not to be automatically determined, the user may manually select it via, for example, a user interface.

At 410, patient signal analysis unit 222 determines continuous cardiac cycles. Continuous cardiac cycles may be determined by, for example, R wave detection using an amplitude threshold for R waves.

At 412, patient signal analysis unit 222 performs actiniform segmentation. Actiniform segmentation may be performed by first detecting an R wave in the continuous cardiac cycles. The R wave peak time is also known as the intrinsicoid deflection, which represents the time taken for excitation to spread from the endocardial to the epicardial surface of the left ventricle of the heart. The R wave may be determined by, for example, a peak detector.

The actiniform segmentation is performed based on an actiniform shape 104 (or distribution), as previously described with reference to FIG. 1. In some implementations, the actiniform shape 104 is defined as a non-uniform radiated form centered at an R wave peak. The actiniform shape 104 may include lines radiating from the center towards key time points of the signal waveform 101. The key time points may be defined based on different waves that occur within a cardiac cycle (e.g., P, Q, R, S, T waves, etc.). Each cardiac cycle may be segmented by the actiniform lines into different portions.

At 414, patient signal analysis unit 222 extracts one or more actiniform parameters of a region of interest (ROI) of the segmented waveform. The region of interest (ROI) may be any portion (e.g., single cardiac cycle for unilateral ratios, two different cycles for bilateral ratios, etc.) of the segmented waveform that is identified for analysis. The one or more actiniform parameters may include any values that may be measured based on the segmented waveform. Types of actiniform parameters include, but are not limited to, angles (e.g., $\alpha 1$, $\alpha 2$, etc.) between actiniform lines, distances between the R-wave peak and the key time points (e.g., $L_Q$, $L_{left}$, $L_R$, etc.), areas (e.g., S1, S2, etc.) between adjacent actiniform lines, and so forth.

At 416, patient signal analysis unit 222 determines one or more unilateral actiniform ratios based on the actiniform parameters. Each unilateral actiniform ratio compares actiniform parameters associated with at least two different portions of a single cardiac cycle (or heart beat) to characterize morphology and detect changes in the waveform of the patient signal. The unilateral actiniform ratios may include an actiniform shape ratio (ASR), an actiniform distance ratio (ADR) and/or an actiniform area or energy ratio (AAER).

An actiniform shape ratio (ASR) may be determined based on angles (e.g., $\alpha 1$, $\alpha 2$, etc.) between actiniform lines that connect the R wave peak to key time points of the signal waveform. In some implementations, the ASR may be determined as follows:

$$ASR_{angle\ calculation-ij} = \frac{\text{Tan}(\alpha_i)}{\text{Tan}(\alpha_j)} \quad (1)$$

$$ASR_{angle-ij} = \frac{\alpha_i}{\alpha_j} \quad (2)$$

wherein $ASR_{angle-ij}$ denotes the actiniform shape ratio of angles $\alpha_i$ and $\alpha_j$, and $ASR_{angle\ calculation-ij}$ denotes the actiniform shape ratio of values derived from trigonometric tangent functions $\text{Tan}(\alpha_i)$ and $\text{Tan}(\alpha_j)$. It should be appreciated that other types of trigonometric functions, such as Sine (or Sin), Cosine (or Cos), etc., may also be used to compare the angles. $\alpha_i$ and $\alpha_j$ denote two different angles in the actiniform segmented waveform, and may be automatically selected by a software algorithm or manually determined by a clinical user according to the clinical application and user preference. For example, as shown in FIG. 1, i and j may be a pair of different values from 1 to 6.

An actiniform distance ratio (ADR) of actiniform line distances $L_i$ and $L_j$ may be determined as follows:

$$ADR_{ij} = \frac{L_i}{L_j} \quad (3)$$

By comparing the actiniform distances, the waveform shape and latency changes of the ROI peaks in the patient signal may be more sensitively and accurately quantified. $L_i$ and $L_j$ denote distances of two different lines in the actiniform segmented waveform, and may be automatically selected by a software algorithm or manually determined by a clinical user according to the clinical application and user preference. For example, as shown in FIG. 1, the actiniform distance can be $L_Q$, $L_{left}$, $L_R$, etc.

The actiniform distance may also be defined as a differential value centered at the distance ($L_R$) from the R wave peak to the zero voltage line, which may highlight and amplify waveform distortions due to cardiac pathologies. The differential version of the ADR may be defined as follows:

$$ADR_{differential\text{-}ij} = \frac{|L_i - L_R|}{|L_j - L_R|} \quad (4)$$

wherein $ADR_{differential\text{-}ij}$ represents the differential ratio of the ROI actiniform distances $L_i$ and $L_j$, centering at R wave actiniform distance $L_R$.

The Actiniform Area and Energy Ratio (AAER) may be used to compare the area size and energy integration within actiniform segmented portions of the signal waveform. In some implementations, the actiniform area and energy ratios are defined as following:

$$AAER_1 = \frac{\int_{A(i) \in S_m} \lambda_m \cdot |A(i)|}{\int_{A(j) \in S_n} \lambda_n \cdot |A(j)|} \quad (5)$$

$$AAER_2 = \frac{\int_{A(i) \in S_m} \lambda_m \cdot |A(i)|^2}{\int_{A(j) \in S_n} \lambda_n \cdot |A(j)|^2} \quad (6)$$

wherein $AAER_1$ and $AAER_2$ denote the actiniform area and energy ratios respectively between two segmented area data sets, $S_m$ and $S_n$; $A(i)$ and $A(j)$ denote amplitude values of the corresponding waveform portions; and $\lambda_m$ and $\lambda_n$ denote coefficients. Theoretically, the signal time durations of cardiac ROI portions are dependent on the cardiac heart rate; however, it may not be proportional. The coefficients $\lambda_m$ and $\lambda_n$ may be used to compensate for these changes due to different heart rates (e.g., 60 or 120 BPM). The actiniform area and energy ratios $AAER_1$ and $AAER_2$ describe waveform changes or distortions, especially in the energy of electrophysiological excitation and transmission in the heart system.

The different unilateral actiniform ratios may be combined to generate a Unilateral Actiniform Integrating Ratio (UAIR) to facilitate monitoring and diagnosis of patient status. The UAIR may be determined as a weighted sum of different unilateral actiniform ratios as follows:

$$\text{Unilateral Actiniform Integrating Ratio } (UAIR) = \sum_{i \in unilateral\_ratios} \delta_i \cdot Ratio_i \quad (7)$$

wherein UAIR denotes the integrated ratio of multiple unilateral ratios; i is an index selected from 1 to the total number of unilateral ratios (unilateral_ratios) and $\delta_i$ is a weighting coefficient for each unilateral actiniform ratio $Ratio_i$.

Further, a statistical index may be generated based on the unilateral actiniform ratios or parameters. The statistical index may include, for example, a Single Actiniform Index Variation (SAIV) or a Single Actiniform Ratio Variation (SARV) that may be determined as follows:

$$SAIV = \frac{\text{mean}(Actiniform\_index_i)}{STD(Actiniform\_index_i)} \quad (8)$$

$$SARV = \frac{\text{mean}(Ratio_i)}{STD(Ratio_i)} \quad (9)$$

wherein $Actiniform\_index_i$ is any defined actiniform parameter in the segmented waveform (e.g., angles, distances, areas, etc., as shown in FIG. 1); $Ratio_i$ is any new calculated actiniform unilateral ratio (e.g., ASR, ADR, AAER, etc.); mean(•) and STD(•) denote averaging and standard deviation operations.

At 418, patient signal analysis unit 222 determines bilateral actiniform ratios based on the actiniform parameters. Each bilateral actiniform ratio compares actiniform parameters associated with portions of at least two different cardiac cycles (or heart beats) to characterize morphology and detect changes in the waveform of the patient signal. In order to obtain stable and accurate sequential time data analysis, a time shifting window may be utilized to cover different sequential cardiac cycles (e.g., 5-10 heart beats). The bilateral actiniform ratios may include, but are not limited to, a Cross Actiniform Index Variation (CAIV) and a Cross Actiniform Ratio Variation (CARV).

A Cross Actiniform Index Variation (CAIV) and a Cross Actiniform Ratio Variation (CARV) may be determined as follows:

$$CAIV = \frac{\text{mean}(Actiniform\_index_i)}{STD(Actiniform\_index_j)} \quad (10)$$

$$CARV = \frac{\text{mean}(Ratio_i)}{STD(Ratio_j)} \quad (11)$$

wherein $Actiniform\_index_i$ and $Actiniform\_index_j$ denote any defined actiniform parameters in different cycles of the segmented waveform (e.g., angles, distances, areas, etc. as shown in FIG. 1); $Ratio_i$ and $Ratio_j$ represent any calculated unilateral actiniform ratios associated with different cycles of the segmented waveform (e.g., ASR, ADR, AAER, etc.) and mean(•) and STD(•) denote averaging and standard deviation calculation operations. CAIV and CARV characterizes mutual variation between two actiniform parameters and ratios.

At 420, patient signal analysis unit 222 determines if pathology or cardiac event detection is to be performed. If not, the method 400 returns to step 410. If yes, the method 400 proceeds to step 422.

Figure 5:
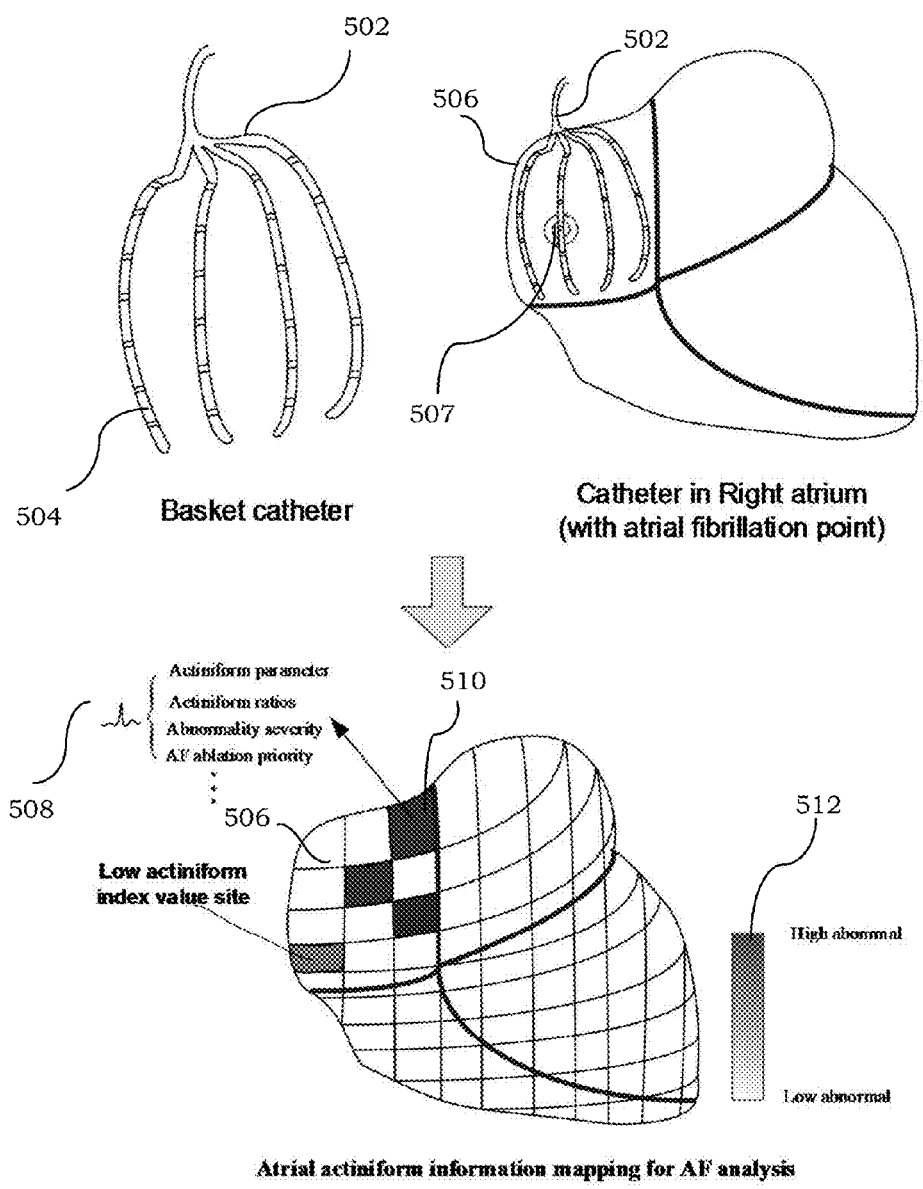
FIG. 5 illustrates an exemplary multi-channel pathology mapping.

At 422, patient signal analysis unit 222 performs multiple-channel pathology mapping. The generated actiniform parameters, ratios, and/or indices may be mapped to corresponding sites of the heart where multi-channel patient signals were acquired. Cardiac events may be detected and characterized based on such pathology mapping. FIG. 5 illustrates an exemplary multi-channel pathology mapping. Atrial fibrillation may be detected based on analysis of multi-channel electrophysiological signals. Actiniform information analysis and mapping is performed based on electrophysiological signals acquired by a multi-channel intra-cardiac electrographic lead system. In this example, a basket catheter 502 with multiple leads 504 is placed in the right atrium of the heart 506. Data from each available lead or site 507 in the atrial chamber is filtered, decomposed and processed to generate output parameters 508, such as actiniform parameters and ratios, location and severity of an abnormality, AF ablation priority, etc. The output parameters may be mapped to a particular local site 510 in the atrial chamber. Sites associated with low actiniform index (e.g., parameter or ratio) values are determined to be less abnormal than sites with high actiniform index values. The mapped sites may be graphically presented as an image at a user interface with colors or shadings 512 that are indicative of the severity of the abnormality. Such actiniform function mapping may be performed in two or three dimensions (2D or 3D). The mapping may be updated in real time based on calculation intervals and timing steps. By using 2D or 3D image technologies with high speed computer systems, actiniform function mapping may be derived in real time and may greatly facilitate clinical doctors in finding abnormalities in cardiac function.

Every atrial chamber site 510 may be characterized by varying the signal position or lead location of the basket catheter 502. Any abnormal atrial rotor or changes in atrial rotor activities may be accurately and precisely scanned, characterized and mapped into the heart structure. The location, timing, severity, type, prediction, etc., of cardiac pathologies and diseases can advantageously be derived earlier and more accurately based on such detailed analysis of waveform distortions in selected ROI areas of actiniform segmented signals. Color (or shading) coded abnormality severity associated with the continuous calculated actiniform ratios may be presented to help the clinical doctor in the clinical evaluation of the cardiac arrhythmia and in determining the correct treatment, such as ablation priority, ablation energy, ablation timing, ablation location, drug delivery, etc.

At 424, patient signal analysis unit 222 may optionally adaptively adjust calculation parameters used for calculating the afore-mentioned actiniform parameters, ratios and/or indices. The adaptive adjustment may be performed automatically, semi-automatically or manually by the clinical user based on clinical experience and knowledge. Such calculation parameters may include, but are not limited to, calculation window size, signal portion, ROI area, time steps, severity thresholds, and so forth.

At 426, patient signal analysis unit 222 generates a patient report. The patient report may record the abnormality, associated characteristics (e.g., location, type, severity, timing, etc.) and other information (e.g., suggested treatment options). The patient report may be in the form of, for example, an alert message presented at patient monitor 230. The patient report may also be stored in database 224 for future retrieval, transmitted or shared with other client computers, and/or printed in physical form for viewing.

Figure 6:
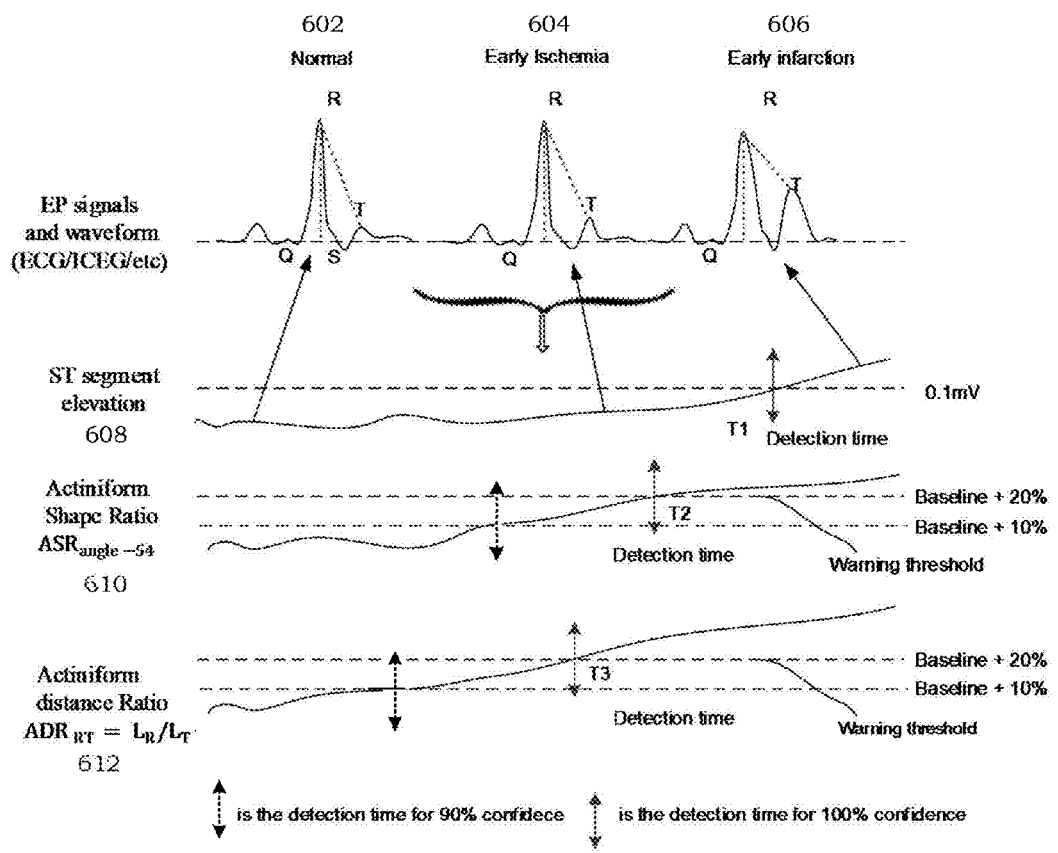
FIG. 6 shows exemplary computer simulation data for myocardial ischemia event detection and characterization.

There may be many kinds of clinical usages and applications that can employ the actiniform segmented patient signals (e.g., surface ECG, intra-cardiac electrograms, etc.) for cardiac abnormality detection and pathology characterization (e.g., myocardial ischemia or infarction). FIG. 6 shows exemplary computer simulation data for myocardial ischemia event detection and characterization. Three episodes of cardiac events are simulated: normal (or healthy) event 602, early stage of myocardial ischemia event 604, and mature myocardial ischemia (or early infarction) event 606. In the three-episode diagnosis, three methods were applied and compared. For effective validation, actiniform shape and distance ratio diagnoses were compared with the traditional ST segment elevation evaluation (clinical gold standard). Since this example is for myocardial ischemia detection, angles $\alpha 5$ and $\alpha 4$ (as defined in FIG. 1) were used in determining the actiniform shape ratio (ASR) and $L_R$ and $L_T$ (as defined in FIG. 1) were selected for determining the actiniform distance ratio (ADR). The ST segment elevation evaluation used a 0.1 mV detection threshold, while 10% and 20% change thresholds were utilized for the actiniform ratio calculation and comparison.

In the ST Segment evaluation 608, there were no obvious changes in the ST segment for early ischemia while ST segment increases more than 0.1 mV after T1 (time for 100% confidence detection). In the actiniform shape ratio diagnosis 610, $ASR_{angle-54}$ value showed that myocardial event can be detected with 100% confidence at T2 (T2 is 10 seconds earlier than T1). In the actiniform distance ratio diagnosis 612, $ADR_{RT}$ detected the myocardial ischemia event at T3, which was 7 seconds earlier than T2. Accordingly, it can be concluded that actiniform ratio analysis is more sensitive and accurate in detecting cardiac arrhythmia detection much earlier than current clinical methods, which may help to detect cardiac events and pathology trend, thereby avoiding fatal cardiac arrhythmia.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A system for patient signal analysis, comprising:
a patient monitor configured to acquire a patient signal data waveform from a patient;
a medical treatment device configured to provide treatment to the patient; and
a computer system communicatively coupled to the patient monitor and the medical treatment device, wherein the computer system includes
a non-transitory memory device for storing computer readable program code, and
a processor in communication with the memory device, the processor being operative with the computer readable program code to perform steps including
performing actiniform segmentation on the patient signal data waveform based on an actiniform shape centered at a peak of the waveform,
extracting actiniform parameters from the segmented patient signal data waveform, determining one or more actiniform ratios based on the actiniform parameters, determining control parameters based on the one or more actiniform ratios, and controlling the medical treatment device by applying the control parameters.

2. The system of claim 1 wherein the medical treatment device comprises a pacing device, an ablator, a cardioverter or a defibrillator.

3. The system of claim 1 wherein the actiniform shape is centered at an R wave peak of the patient signal data waveform.

4. The system of claim 1 wherein the actiniform shape comprises connection lines extending from the peak to key time points of the patient signal data waveform.

5. The system of claim 4 wherein at least one of the key time points is defined by a P wave, Q wave, R wave, S wave or T wave.

6. The system of claim 4 wherein at least one of the key time points is defined at a time point before a P wave or after a T wave.

7. The system of claim 1 wherein the patient monitor comprises a multi-channel intra-cardiac electrographic lead system.

8. A computer-implemented method of patient signal analysis, comprising:

performing, by a processor, actiniform segmentation on patient signal data waveform based on an actiniform shape centered at a peak of the waveform, wherein the actiniform shape includes connection lines extending from the peak to key time points of the patient signal data waveform;

extracting, by the processor, actiniform parameters from the segmented patient signal data waveform; and determining, by the processor, one or more actiniform ratios based on the actiniform parameters to monitor changes in the patient signal data waveform.

9. The method of claim 8 wherein performing the actiniform segmentation comprises:

detecting an R wave peak in the patient signal data waveform;

defining the actiniform shape centered at the R wave peak; and segmenting the patient signal data waveform into multiple different portions using the actiniform shape.

10. The method of claim 8 wherein at least one of the key time points is defined by a P wave, Q wave, R wave, S wave or T wave.

11. The method of claim 8 wherein at least one of the key time points is defined at a time point before a P wave and/or after a T wave.

12. The method of claim 8 wherein the actiniform parameters comprise angles, distances or areas.

13. The method of claim 8 wherein the one or more actiniform ratios comprise a unilateral actiniform ratio.

14. The method of claim 13 wherein the unilateral actiniform ratio comprises an actiniform shape ratio.

15. The method of claim 13 wherein the unilateral actiniform ratio comprises an actiniform distance ratio.

16. The method of claim 13 wherein the unilateral actiniform ratio comprises an actiniform area ratio.

17. The method of claim 13 wherein the unilateral actiniform ratio comprises an actiniform energy ratio.

18. The method of claim 8 wherein the one or more actiniform ratios comprise a unilateral actiniform integrating ratio that includes a weighted sum of different unilateral actiniform ratios.

19. The method of claim 8 wherein the one or more actiniform ratios comprise a single actiniform index variation.

20. The method of claim 8 wherein the one or more actiniform ratios comprise a single actiniform ratio variation.

21. The method of claim 8 wherein the one or more actiniform ratios comprise a bilateral actiniform ratio.

22. The method of claim 21 wherein the bilateral actiniform ratio comprises a cross actiniform index variation.

23. The method of claim 21 wherein the bilateral actiniform ratio comprises a cross actiniform ratio variation.

24. The method of claim 8 further comprises mapping the one or more actiniform ratios to corresponding sites of a heart.

25. A non-transitory computer readable medium embodying a program of instructions executable by machine to perform steps for cardiac function characterization, the steps comprising:

detecting an R wave peak of a patient signal data waveform;

performing actiniform segmentation on the patient signal data waveform based on an actiniform shape centered at the R wave peak, wherein the actiniform shape includes connection lines extending from the R wave peak to key time points of the patient signal data waveform;

extracting actiniform parameters from the segmented patient signal data waveform; and determining one or more actiniform ratios based on the actiniform parameters to monitor changes in the patient signal data waveform.

\* \* \* \* \*